United States Patent
Leschinsky

(10) Patent No.: US 9,717,420 B2
(45) Date of Patent: Aug. 1, 2017

(54) IMPLANTABLE APPARATUS FOR FACILITATING IMAGING-BASED DIAGNOSES

(75) Inventor: Boris Leschinsky, Mahwah, NJ (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 607 days.

(21) Appl. No.: 13/128,627

(22) PCT Filed: Dec. 20, 2010

(86) PCT No.: PCT/US2010/061295
§ 371 (c)(1),
(2), (4) Date: May 10, 2011

(87) PCT Pub. No.: WO2012/087277
PCT Pub. Date: Jun. 28, 2012

(65) Prior Publication Data
US 2012/0158038 A1    Jun. 21, 2012

(51) Int. Cl.
| | | |
|---|---|---|
| A61B 5/02 | (2006.01) | |
| A61B 5/0215 | (2006.01) | |
| A61B 5/01 | (2006.01) | |
| A61B 5/00 | (2006.01) | |
| A61B 6/12 | (2006.01) | |
| A61B 8/08 | (2006.01) | |
| A61F 2/07 | (2013.01) | |

(52) U.S. Cl.
CPC .............. *A61B 5/0215* (2013.01); *A61B 5/01* (2013.01); *A61B 5/6876* (2013.01); *A61B 5/6862* (2013.01); *A61B 6/12* (2013.01); *A61B 8/0841* (2013.01); *A61F 2/07* (2013.01)

(58) Field of Classification Search
CPC ....... A61B 5/021; A61B 5/0215; A61B 5/031; A61F 2/07; G01K 5/62; G01K 5/36; G01K 5/40; G01K 5/42; G01K 5/54; G01K 5/50; G01K 5/48; G01K 5/483; G01K 5/52; G01K 5/58; G01K 5/56; G01K 5/64; G01K 5/60; G01K 5/66; G01K 5/70; G12B 1/00; G12B 1/02; G12B 1/04
USPC .................................................. 600/486, 485
See application file for complete search history.

(56) References Cited

U.S. PATENT DOCUMENTS

| | | | | |
|---|---|---|---|---|
| 1,970,219 | A | * | 8/1934 | Bloch ...................... G01K 5/62 374/146 |
| 2,411,093 | A | * | 11/1946 | Jameson ...................... 337/351 |
| 4,127,110 | A | * | 11/1978 | Bullara ........................ 600/561 |
| 5,564,434 | A |  | 10/1996 | Halperin et al. |

(Continued)

OTHER PUBLICATIONS

Webster, The Measurement Instrumentation and Sensors Handbook, CRC Press, 1999, pp. 32-2 to 32-4.*

(Continued)

*Primary Examiner* — Michael Kahelin
*Assistant Examiner* — Tho Tran
(74) *Attorney, Agent, or Firm* — Maschoff Brennan

(57) ABSTRACT

Implantable apparatuses or biosensors for facilitating imaging-based diagnoses and methods thereof are disclosed. An implantable apparatus is configured to exhibit a form when subjected to a first physical parameter indicative of a first physiological state, and a second form when subjected to a second physical parameter indicative of a second physiological state.

11 Claims, 10 Drawing Sheets

(56) References Cited

U.S. PATENT DOCUMENTS

| | | | |
|---|---|---|---|
| 5,935,084 A * | 8/1999 | Southworth | 600/561 |
| 6,669,647 B2 | 12/2003 | Letort et al. | |
| 7,426,413 B2 | 9/2008 | Balczewski et al. | |
| 2001/0021873 A1 * | 9/2001 | Stinson | 623/1.34 |
| 2004/0043206 A1 * | 3/2004 | Bush et al. | 428/297.4 |
| 2005/0192512 A1 * | 9/2005 | Butterworth | 600/549 |
| 2007/0112413 A1 * | 5/2007 | Smith | 623/1.13 |
| 2007/0225633 A1 | 9/2007 | Ferren et al. | |
| 2007/0293904 A1 * | 12/2007 | Gelbart | A61N 1/3785 607/35 |
| 2009/0131930 A1 * | 5/2009 | Gelbart | A61B 18/1492 606/41 |
| 2009/0259301 A1 * | 10/2009 | Gelbart | A61F 2/07 623/1.42 |

OTHER PUBLICATIONS

International Search Report and Written Opinion, mailed Mar. 18, 2011 for PCT/US10/61295.
Golzarian J, Valenti D. Endoleakage after endovascular treatment of abdominal aortic aneurysms: diagnosis, significance and treatment. Eur Radiol 2006; 16(12):1849-57.
www.fda.gov/cdrh/pdf6/K061046.pdf, CardioMEMS EndoSure Wireless AAA Pressue Measurement System, Oct. 12, 2006.
Sonesson B, Dias N, Malina M et al. Intra-aneurysm pressure measurement in successfully excluded abdominal aortic aneurysm after endovascular repair. J Vasc Surg 2003; 37:733-8.
Dias NV, Ivancev K, Malina M et al. Intra-aneurysm sac pressure measurements after endovascular aneurysm repair differences between shrinking, unchanged, and expanding aneurysms with and without endoleaks. J Vasc Surg 2004; 39:1229-35.
Ohki T, Ouriel K, Silveira PG et al. Initial results of wireless pressure sensing for endovascular aneurysm repair: the APEX Trial—Acute Pressure Measurement to Confirm Aneurysm Sac EXclusion. J Vasc Surg 2007; 45(2):236-42.
Ellozy SH, Carroccio A, Lookstein RA et al. Abdominal aortic aneurysm sac shrinkage after endovascular aneurysm repair: correlation with chronic sac pressure measurement. J Vasc Surg 2006; 43(1):2-7.
Silveira PG, Miller CW, Mendes RF et al. Correlation between intrasac pressure measurements of a pressure sensor and an angiographic catheter during endovascular repair of abdominal aortic aneurysm. Clinics 2008; 63(1):59-66.
Hoppe H, Segall JA, Liem TK et al. Aortic aneurysm sac pressure measurements after endovascular repair using an implantable remote sensor: initial experience and short-term follow-up. Eur Radiol 2008; 18(5):957-65.
Ostrovsky, G,M "ImPressure122 Sensor," MedGadget, accessed at http://www.medgadget.com/2006/03/impressure_sens_1.html, Mar. 10, 2006, pp. 1-3.
Richardson, N.M "Innovation: CardioMEMS EndoSure Sensor," accessed at http://web.archive.org/web/20100515173136/http://www.inc.com/magazine/20090601/innovation-cardiomems-endosure-sensor.html, Jun. 1, 2009, pp. 1-2.

\* cited by examiner

IMPLANTABLE APPARATUS FOR FACILITATING IMAGING-BASED DIAGNOSES

CROSS-REFERENCE TO RELATED APPLICATIONS

This application is a U.S. National phase entry under 35 U.S.C. §371 of International application No. PCT/US2010/061295, filed on Dec. 20, 2010, which is incorporated herein by reference in its entirety.

BACKGROUND

An abdominal or thoracic aortic aneurysm is a condition in which a portion of the aorta wall is weakened and expands over time, thereby forming an aneurysmal sac. At some point, the aneurysmal sac may rupture and cause major bleeding. Patients with a ruptured aneurysm have a very high mortality rate. Modern imaging techniques allow for early diagnosis of an aneurysm. Early diagnosis, along with an aging population, may increase the number of patients diagnosed with an aneurysm over the coming years.

Aneurysms may be surgically excised and replaced with a synthetic graft when the aneurysmal sac reaches a diameter of approximately five centimeters in diameter. The surgical resection of an aneurysm is highly durable but also highly invasive. The patient typically stays in the hospital for a few days and recovers at home for a month or longer. Surgical resection of an aneurysm can result in various complications.

The endovascular repair of aneurysms has been developed. During this procedure, an expandable stent/graft is deployed with an endoscope. The deployed stent/graft spans the aneurysmal sac and overlaps with healthy portions of the aorta; successful insertion of a stent/graft excludes the aneurysmal sac from exposure to aortic blood pressure, and a thrombus forms in the sac over time. This approach is less-invasive than traditional resection; the hospital stay is shortened and recovery is faster. Endovascular repair can be performed on some patients who cannot undergo a traditional surgery due to age limitations or for other reasons.

Failure of the stent/graft to completely exclude the aneurysm from aortic blood pressure may result in continued pressurization of the aneurysmal sac, and may result in eventual rupture and bleeding. There are several factors that may result in aneurysmal sac pressure after stent/graft implantation. These include graft-related factors—such as the presence of endoleaks, graft porosity, and graft compliance—as well as anatomic factors, such as continuing patency of the aneurysm side branches, misfit of the stent/graft to the aorta, the aneurysm morphology, and characteristics of the aneurysm thrombus. Endoleaks—persistent perfusion of the aneurysmal sac—are variously reported to result in anywhere from 10% to 50% of cases.

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

The present disclosure describes a device for facilitating imaging diagnoses. Some example devices may include an implantable apparatus. The implantable apparatus is configured to exhibit a first form when subjected to a first physical parameter indicative of a first physiological state, and to reversibly exhibit a second form when subjected to a second physical parameter indicative of a second physiological state. The first physiological state may be a healthy state and the second physiological state may be a diseased state. The first form may be within a first range of forms, the second form may be within a second range of forms. The first physical parameter may be within a first range of physical parameters, and the second physical parameter may be within a second range of physical parameters.

The second range of forms may be separated by an intermediate range of forms indicative of an alternative or intermediate physiological state. The first form may be a first size, and the second form may be a second size. Also, the first form may be a first shape, and the second form may be a second shape.

The first physical parameter may be a first pressure, and the second physical parameter may be a second pressure. The first pressure may be between 0 and 10 millimeters of mercury, and the second pressure may be between 50 and 150 millimeters of mercury. The first physical parameter may be a first temperature, and the second physical parameter may be a second temperature. The first temperature may be between 97 and 99 degrees Fahrenheit, and the second temperature may be between 101 and 105 degrees Fahrenheit. A difference between the first form and the second form may correlate to a difference between the first physical parameter and the second physical parameter.

The implantable apparatus may comprise a bi-material strip. In another embodiment, the implantable apparatus may comprise a sealed bellows. The implantable apparatus may comprise a sealed housing and a plunger partially within the housing. The implantable apparatus may comprise a helical coil wire having an indicator wire attached to ends of the helical coil wire. The ends of the helical coil wire may remain aligned when the implantable apparatus is subjected to the first physical parameter such that the indicator wire remains substantially straight. And the ends of the helical coil wire may rotate relative to one another when the implantable apparatus is subjected to the second physical parameter such that the indicator wire wraps around the helical coil wire.

A difference between the first form and the second form may be discernable using one or more of ultrasound imaging, X-Ray, fluoroscopy, CT, and MRI.

Also described is a method for determining a physiological state of an animal or human subject. An area of the animal or human subject where an implantable apparatus has been implanted may be imaged. It may be determined whether the implantable apparatus visualized by said imaging exhibits a first form indicative of a first physical parameter indicative of a first physiological state, or a second form indicative of a second physical parameter indicative of a second physiological state. The method may also include comparing an image of the area to a baseline image showing a baseline form of the implantable apparatus. The first form may be a first size, and the second form may be a second size. The first form may be a first shape, and the second form may be a second shape. The first physical parameter may be a first pressure, and the second physical parameter may be a second pressure. The first pressure may be between 0 and 10 millimeters of mercury, and the second pressure may be between 50 and 150 millimeters of mercury. The first physical parameter may be a first temperature, and the second physical parameter may be a second temperature.

The first temperature may be between 97 and 99 degrees Fahrenheit, and the second temperature may be between 101 and 105 degrees Fahrenheit.

The first form may be within a first range of forms, and the second form may be within a second range of forms. The first physical parameter may be within a first range of physical parameters, and the second physical parameter may be within a second range of physical parameters.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1A:
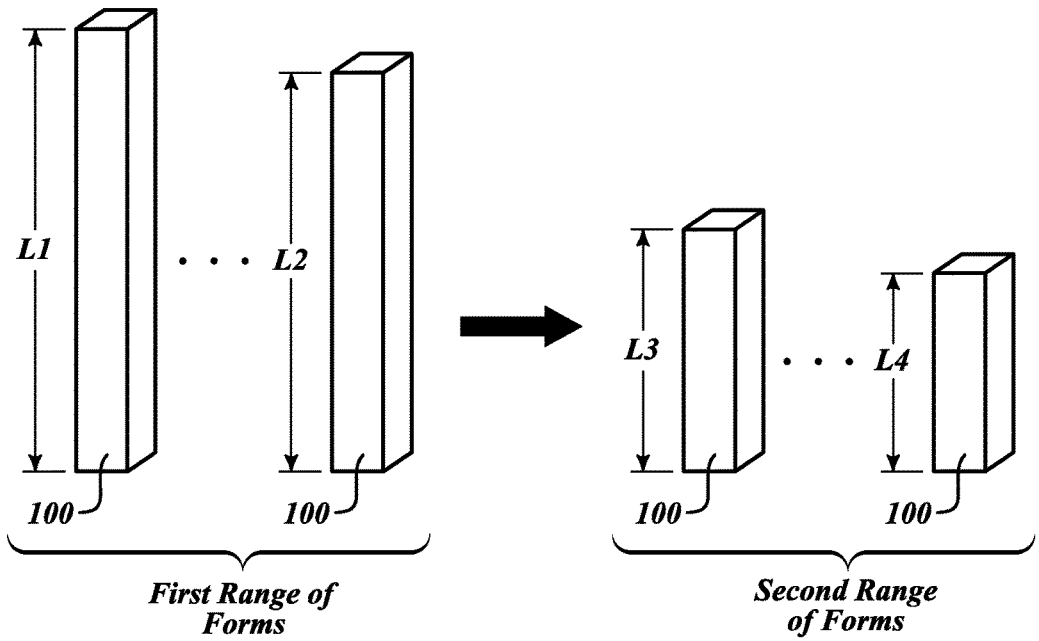
FIGS. 1A and 1B illustrate block diagrams of implantable apparatuses having forms changeable upon exposure to various ranges of physical parameters.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

This disclosure is drawn, among other things, to methods, devices, and apparatuses for facilitating the imaging-based diagnoses of a physiological state in a human or animal subject using an implantable apparatus or biosensor. Changes in the physical form, such as but not limited to the shape, length, width, or size, of at least a portion of the implantable apparatus may indicate a physiological state of the human or animal subject, such as the physiological state of a localized area (such as an aneurysm in an aorta or other blood vessel) of a human or animal subject. A localized area may be an area of local inflammation where there may be a local increase in temperature indicative of an inflammatory process. This may be anywhere in the body such as but not limited to the central trunk section where the major organs are located. An implantable apparatus may change in size, length, and/or shape in response to various physical parameters (such as temperature and/or pressure). Some portions of implantable apparatuses according to the present disclosure may be designed to respond to changes in physiological conditions by changing shape while other portions may be designed to not change shape. In some embodiments, various portions may be designed to change shape or form in response to a change in one type of physiological condition (such as a change in pressure), and others to a change in another type of physiological condition (such as a change in temperature). Portions according to embodiments may be designed for adherence to a stent or a localized area of a human or animal subject's anatomy (such as an aneurysm); such portions may be composed of materials that do not change shape in response to the changes in physiological conditions. These concepts will be further elaborated in the description that follows.

The implantable apparatus may be imaged to determine its form (such as but not limited to its size, length, and/or shape) in order to identify a physiological state and/or a change in a physiological state. In embodiments, an image of the implantable apparatus may be compared to a baseline or reference image in order to determine its form and/or any changes in its form. A baseline or reference image may be an image of a deployed implantable apparatus taken at the time that the baseline image is or was captured, or shortly thereafter such as in the minutes or hours after deployment of the implantable apparatus. A baseline or reference image may also be an image of the same or similar implantable apparatus when exposed to various physiological stimuli externally (outside of the human or animal subject). The baseline or reference image may also be a comparison image, such as an image of the same or similar implantable apparatus exposed to various physiological stimuli in use in another animal or human subject. The baseline or reference image may also be taken at some arbitrary time after implantation in the human or animal subject, such as to re-establish a new steady-state of the implantable apparatus to correspond to a new steady-state physiological condition of the human or animal subject. The implantable apparatus may be assumed to have a baseline form at the time of implantation. In other words, the baseline form may be the form of the apparatus at the time that the apparatus is implanted. A new image of the apparatus may be taken at a later time when the physiological state of the human or animal subject is unknown. The new image may be compared to the baseline image in order to determine whether the new image of the implantable apparatus shows that the deployed implantable apparatus has a form that differs sufficiently from the form of the apparatus shown in the baseline image as can be detected for example using provided reference images. Two states of the sensor (indicating for example normal and diseased conditions) may be reflective of significantly different physical states of the organ environment, as is described elsewhere within this Detailed Description. Calibration (e.g. baseline and/or reference) images may be provided to make sure a user understands the meaning of a particular shape and/or form of an imaged implanted apparatus. If the form and/or shape of the implantable apparatus shown in the new image are different from the baseline image, it may be determined by the user that the physical parameters that the implantable apparatus is subjected to may have also changed from the time that the baseline image was taken. Thus, comparing the new image to the baseline image may assist a clinician, technician, doctor, nurse, or other person in determining whether the physical parameters, and therefore the physiological state of the human or animal subject, have changed.

It may be possible for the viewing angle or orientation of the device to alter the appearance of the device when the device is imaged. In embodiments, one end of the device may have a known reference shape such as a small flat circle or other shape. An image of the device may show the circle (or other shape) in a plain or skewed form which may be used to interpret the relative viewing angle and/or orientation of the sensor. If it is determined that the device has been imaged at an angle, the device may be re-imaged with a different orientation, or the person viewing the image may make a judgment regarding the shape of the sensor based on the determined relative viewing angle, or the person viewing the new image may simply decide that the image is inconclusive with regard to the physiological condition of the human or animal subject. In other embodiments, computer modeling may be used to predict the shape of the implantable apparatus and then compare it to one or more baseline and/or reference images or shapes.

As described in more detail below, an implantable apparatus may be configured to exhibit a first form when subjected to a first physical parameter indicative of a first physiological state and to exhibit a second form when subjected to a second physical parameter indicative of a second physiological state. In embodiments described herein, the forms, physical parameters, and physiological states may be defined by ranges of forms, parameters, and states as described in more detail below. Forms within the first and the second range of forms may be distinguishable from one another when imaged, such as when imaged with a conventional medical imaging technique such as but not limited to ultrasound, X-Ray, fluoroscopy, CT, MRI. In this way, the implantable apparatus may facilitate the diagnosis of a physiological state by medical imaging.

Physiological states that may be diagnosed with implantable apparatuses according to embodiments may include but are not limited to hypertension, hypotension, an endoleak of a stent/graft deployed around an aneurysmal sac, fever, infection, hypothermia, or inflammation. An example endoleak may be an endoleak that has formed around a stent/graft deployed in an artery, such as in an aortic aneurysmal sac. An "endoleak" is a compromised stent/graft that results in blood flowing into the aneurysmal sac from an artery such as the aorta, despite the presence of the stent/graft. An endoleak is important to detect because there is a danger that an aneurysmal sac exposed to aortic blood pressures will rupture and cause the patient to bleed out. An example infection may be a systemic infection, such as influenza, common cold, or other. Detecting a global fever may be a simple matter of checking the subject's temperature. But local inflammation or infection may be much more difficult to detect than systemic infection since body temperature as a whole may not go up due to a localized infection or inflammation. This invention may, therefore, be particularly useful for detecting localized infections. An example localized infection may include, but is not limited to those in the vicinity of the placement of foreign objects such as but not limited to vascular grafts, wounds (natural or medically-induced such as through surgery), including various implants and prosthetics. In some embodiments, localized infections may occur as a result of the introduction of an infectious agent during stent/graft deployment. An infectious agent need not be introduced during deployment of a stent or some other foreign object; the source of infection may instead be introduced later and find the area of the deployed foreign object to be an environment conducive to growth.

The implantable apparatus may be configured such that its form alters in response to physical parameters such as temperature or pressure. The implantable apparatus may exhibit various ranges of forms upon being subjected to various ranges of temperatures and/or various ranges of pressures. These various ranges of temperatures and/or pressures may be indicative of one or more physiological states, such as a diseased state. Ultrasound, X-Ray, fluoroscopy, CT, MRI may be used to image the implantable apparatus and to determine the shape/size/length of the implantable apparatus and thus the physiological state of the human or animal subject. For example, as described elsewhere within this Detailed Description, an image of an implantable apparatus may be compared to a baseline and/or reference image in order to determine a relative size and/or shape of the implantable apparatus.

Implantable apparatuses according to embodiments may indicate blood pressure when deployed in a blood vessel. Implantable apparatuses according to embodiments may be configured to be placed in an aorta or other blood vessel, such as for example in an aneurysmal sac of an abdominal or thoracic aortic aneurysm, or more particularly in an aortic aneurysmal sac, following stent/graft deployment to repair an aneurysm. Such an implantable apparatus may be configured to detect hypertension. Such an implantable apparatus may alternatively be configured to indicate the presence of an endoleak by exhibiting a reduced length in response to increased pressure inside an aneurysmal sac. The implantable apparatus may also bend or twist in response to a change in temperature which may, for example, indicate the presence of a systemic or localized infection.

Implantable apparatuses according to embodiments may be configured to detect a localized physiological condition, such as an endoleak in an aneurysmal sac, and in particular an aortic aneurysmal sac, such as an abdominal aortic aneurysmal sac. Implantable apparatuses according to embodiments may be configured to detect a localized physiological condition, such as an infection in a localized area of the body. A localized infection may be distinguished from a systemic infection in that a localized infection may exist only in a certain portion of an animal or human subject's physiology, such as but not limited to in a blood vessel, aneurysmal sac, organ, gland, joint, or other portion of the human or animal subject's body, or in the vicinity of an implant, surgical site, or wound. In such localized infections, the temperature of the localized portion may be elevated without necessarily significantly elevating the overall body temperature of the animal or human subject.

When diagnosing the presence of certain physiological states such as the presence of an endoleak, there may be no need to determine an actual pressure inside the aneurysmal sac. Rather, it may be sufficient to determine that the pressure inside the aneurysmal sac is within a range of vascular pressures indicative of an endoleak. Implantable biosensors according to embodiments may, therefore, be configured to exhibit a first range of forms when subjected to, for example, a low baseline range of pressures, and a second range of forms when subjected to, for example, a range of high pressures, such as for example aortic pressures as discussed in more detail below. Forms within the first range of forms may be distinguishable from forms within the second range of forms when the apparatus is imaged using one or more medical imaging techniques, such as conventional medical imaging techniques. In this way, the implantable apparatus may facilitate the diagnosis of an endoleak or other physiological conditions.

In regards to embodiments of implantable apparatuses configured to facilitate diagnosis of an endoleak in an aortic aneurysmal sac, such implantable apparatuses may be configured to exhibit a first length when subjected to a low baseline pressure, which may be within a first range of pressures, such as may exist in an aneurysmal sac having a stent/graft with no endoleak. Such a low baseline pressure may be in non-limiting example, below 20, 15, or 10 millimeters of mercury and may correspond to interstitial pressures (the pressure of interstitial fluids such as plasma and other fluids that surround tissues in an animal or human subject). The implantable apparatus may be configured to shorten to one or more absolute second lengths when subjected to a second pressure, which may be within a second range of pressures. A second pressure may be in non-limiting example between 50 and 150 millimeters of mercury, or alternatively above 25, 50, or 75 millimeters of mercury. Such shortened second lengths may be discernable from the first lengths when an image of the device is compared to one or more of a baseline, reference, or comparison image as is described elsewhere within this Detailed Description. For the difference in lengths, shape, or size to be discernable using modern imaging techniques, there may be a gap between the low end of the high pressure range and the high end of the low pressure range over which the device is expected to be subjected to.

Pressure changes may include, for example, a change in fluid pressure exerted on an implantable apparatus. A fluid pressure may be the force per unit area applied by a fluid in a perpendicular direction on the surface of an object, such as an implantable apparatus. For example, an implantable apparatus deployed in an aneurysmal sac that has been repaired with a stent graft may be subjected to either interstitial pressure if there is no endoleak (i.e., the stent graft has not been compromised) or the deployed implantable apparatus may be subjected to the range of vascular pressures (indicative of a compromised stent graft). The range of vascular pressures may be defined by the ranges of pressure exerted during the cardiac cycle of the human or animal subject into which the implantable apparatus has been deployed. The range of pressures exerted during the cardiac cycle may depend on individual variations between human and animal subjects (both between individuals of a single species, as well as between species). But in human subjects, such ranges may for example be as low as 50 millimeters of mercury (or even lower depending on the individual) corresponding to the diastole of the cardiac cycle and as high as 150 millimeters of mercury (or even higher depending on the individual) corresponding to the systole of the cardiac cycle. Interstitial pressure ranges may be anywhere from 0 to 10 millimeters of mercury.

It may be useful to select materials such that the resultant implantable apparatus will not be compressed beyond the material's elastic limit at the high end of the range of pressures for which the apparatus is designed, so as not to cause permanent deformation of the implantable apparatus which may prevent shape recovery when the pressure is removed or lowered (i.e., when the pressure falls back to the low range of pressures). Nitinol and stainless steel are two example materials that could be selected; other example materials are described below. Embodiments may be configured to be attached or adhered to a stent graft for simultaneous deployment. For example, devices according to embodiments may be stapled, sutured, embedded within the stent or graft structure, crimped to the stent graft structure, or placed within the folds of the graft to be outside of the aortic lumen when deployed.

In regards to an implantable apparatus that may be configured to facilitate the diagnosis in human children (such as newborns, infants, toddlers, pre-teens, teenagers), human adult, and/or animals (at various stages of development) of a hypothermic condition, or a localized or systemic infection, such embodiments may be configured to exhibit a degree of curvature within a first range of degrees of curvature (such as but not limited to less than 5, 10, or 15 degrees) when subjected to a baseline temperature, such as a normal body temperature. A baseline temperature may be within a range of temperatures. Such a baseline range of temperatures may be, for example, between 97 and 99 degrees Fahrenheit (for apparatuses configured to detect a fever) or between 90 and 95 degrees Fahrenheit (for apparatuses configured to detect a hypothermic condition). The implantable apparatus may be configured to exhibit a degree of curvature within a second range of degrees of curvature (such as but not limited to greater than 10, 15, or 20 degrees) when subjected to a temperature range, such as for example between 101 and 105 degrees Fahrenheit (for apparatuses configured to detect a fever) or between 97 and 99 degrees Fahrenheit (for apparatuses configured to detect a hypothermic condition). This may leave an intermediate range of temperatures—between 99 and 101 degrees Fahrenheit or between 95 and 97 degrees—that corresponds to an intermediate range of degrees of curvature. Devices for use in animals may facilitate diagnosis over physiological ranges appropriate to the animals' physiology, which may differ from human physiology. As is described in more detail below, properties of the implantable apparatus may be selected such that a difference between the endpoints of the intermediate range of curvatures is discernable using an imaging technique, such as for example conventional imaging techniques. For example, an image of the implantable apparatus may be compared to a baseline, reference, or comparison image of the implantable apparatus as is described elsewhere within this Detailed Description. A discernable change may be, for example, a difference in degree of curvature greater than 10, 15, or 20 degrees. The material type, thickness, or other properties of the implantable apparatus may be chosen such that the implantable apparatuses bend to a significant degree over this intermediate range of temperatures such that endpoints of the intermediate range of curvatures are discernable when imaged.

Other embodiments of an implantable apparatus that may be configured to facilitate the diagnosis of a localized or systemic infection and/or inflammation may be configured to exhibit a degree of twisting (such as but not limited to greater than 10, 15, or 20 degrees of twisting) within a first range of degrees of twisting when subjected to a low baseline temperature, such as a normal body temperature. As with embodiments that exhibit curvature when subjected to temperature changes, a baseline temperature may be within a range of temperatures. Such a baseline range of temperatures may be, for example, between 97 and 99 degrees Fahrenheit (for apparatuses configured to detect a fever) or between 90 and 95 degrees Fahrenheit (for apparatuses configured to detect a hypothermic condition). The implantable apparatus may be configured to exhibit a degree of twisting within a second range of degrees of twisting when subjected to a temperature range, such as for example between 101 and 105 degrees Fahrenheit (for apparatuses configured to detect a fever) or between 97 and 99 degrees (for apparatuses configured to detect a hypothermic condition). This may leave an intermediate range of temperatures—between 99 and 101 degrees Fahrenheit or between 95 and 97 degrees—that corresponds to an intermediate range of degrees of twisting. As discussed in more detail below, properties of the implantable apparatus may be selected such that a difference between the endpoints of the intermediate range of twisting is discernable using an imaging technique, such as for example conventional imaging techniques. The material type, thickness, or other properties of the implantable apparatus may be chosen such that the implantable apparatuses twist to a significant degree over this intermediate range of temperatures such that endpoints of the intermediate range of twisting are discernable when imaged.

Implantable apparatuses according to embodiments may include one or more biocompatible metals such as, but not limited to, nitinol, titanium, stainless steel, various noble metals (such as but not limited to platinum, and gold). Implantable apparatuses may include other biocompatible substances, such as plastic, and may be coated with a biocompatible substance (such as, but not limited to polyurethane). For implantable apparatuses configured as a bellows (as described in more detail elsewhere within this Detailed Description), a polymer with a well-defined elastic compression curve may be used.

Implantable apparatuses according to embodiments may be configured to be implanted percutaneously (via a needle) and/or transcutaneously/subcutaneously (through/under the skin). Implantable apparatuses according to embodiments may be configured to be navigated through various bends in a vascular tree of a human or animal subject via an endoscope, such as for example via the same endoscope used for repair of an aneurysmal sac. Other endoscopes or other devices may also be used, such as a catheter, tube, cannula, or trocar. Various delivery systems may be used. During insertion/implantation of an implantable apparatus, a guidewire may be used along with a dilator. The implantable apparatus may be directed toward the area of interest, where the apparatus is intended to be implanted.

In some embodiments, the largest diameter or greatest width of an implantable apparatus may be approximately 2 to 4 millimeters (mm), or 6 to 12 French (Fr), which may be within the scope of catheter sizes used, for example, in endovascular aneurysm repair. The length of an implantable apparatus or biosensor may be approximately 0.3 to 1.3 inches, such as for example 0.5 to 0.7 inches or 0.8 to 1 inch. It will be appreciated that implantable apparatuses may vary from these ranges without departing from the scope of embodiments disclosed herein. In general, smaller diameter and length apparatuses may be used for implantation in infants or children. If it is anticipated that MRI will be used to image a metallic implantable apparatus, a smaller apparatus may be safer. Longer lengths may provide more accuracy in embodiments where more accurate pressure determinations are needed or desirable (such as determining a degree of hypertension).

In embodiments, an implantable apparatus may exhibit a relatively long length, such as for example 0.5 inches to 5 inches when subjected to a low pressure range (such as for example 0 to 10 millimeters of mercury), and a relatively shorter length, such as for example 0.1 to 0.5 inches, when subject to a high pressure range. Embodiments may be composed of various materials as described above.

Figure 1B:
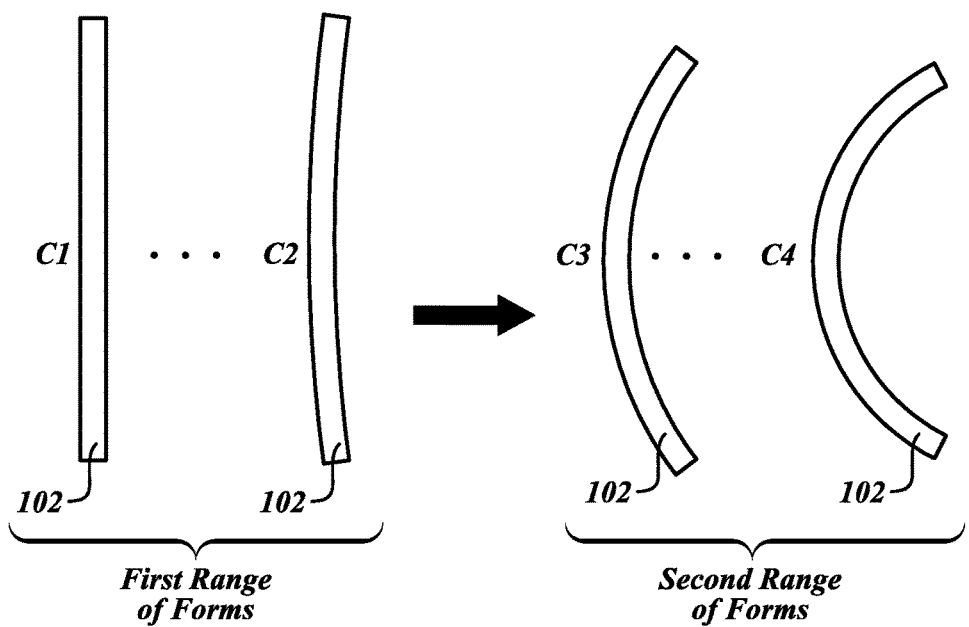

FIGS. 1A and 1B illustrate block diagrams of implantable apparatuses having forms changeable upon exposure to various ranges of physical parameters, such as physical parameters described elsewhere within this Detailed Description. The implantable apparatus may be configured to exhibit a form within a first range of forms—depicted in FIG. 1A as a range of lengths between L1 and L2—upon being subjected to a physical parameter within a first range of physical parameters indicative of a first physiological state. The implantable apparatus may be configured to exhibit a second form within a second range of forms—depicted in FIG. 1A as a range of lengths between L3 and L4—when subjected to a physical parameter within a second range of physical parameters indicative of a second physiological state.

The first physiological state may be a healthy state, such as the absence of an endoleak in a deployed stent/graft; and the second physiological state may correspond to a diseased state, such as for example the presence of an endoleak in a deployed stent/graft. It will be appreciated that physiological states other than the presence of an endoleak in a deployed stent/graft may be indicated by the form, or length, of implantable apparatus 100.

The first range of forms and the second range of forms may be separated by an intermediate range of forms indicative of an alternative or intermediate physiological state. For example, implantable apparatus 100 may be configured to exhibit an intermediate range of forms between length L2 and length L3 when subjected to an intermediate range of physical parameters.

For example, embodiments of implantable apparatus 100 may be configured to facilitate diagnosis of an endoleak in an aneurysmal sac. In such embodiments, implantable apparatus 100 may be configured to exhibit a length between L1 and L2 when subjected to a low baseline range of pressures, such as may exist in an aneurysmal sac having a stent/graft with no endoleak. Such a low baseline range of pressures may be, for example, between 0 and 10 millimeters of mercury. Implantable apparatus 100 may be configured to exhibit a length between L3 and L4 when subjected to a range of vascular pressures, such as for example between 50 and 150 millimeters of mercury. This may leave an intermediate range of pressures—for example between 10 and 50 millimeters of mercury—that may correspond to an intermediate range of lengths of implantable apparatus 100 between L2 and L3. Properties of implantable apparatus 100 may be selected such that the actual size of the apparatus or, for example, a difference between L2 and L3, is discernable using an imaging technique, such as conventional imaging techniques. For example, the material type, thickness, or other properties of implantable apparatus 100 may be chosen such that lengths within the first range of lengths of implantable apparatus 100 are distinguishable or discernable from lengths in the second range of lengths when implantable apparatus 100 is imaged using imaging techniques described elsewhere within this Detailed Description.

Implantable apparatus 100 may be configured to exhibit various lengths or sizes responsive to various physical parameters indicative of various physiological states. Implantable apparatuses according to embodiments may also be configured to exhibit various shapes or ranges of shapes when exposed to various physical parameters. For example, FIG. 1B illustrates implantable apparatus 102. Implantable apparatus 102 may be configured to exhibit a first form within a first range of forms—depicted in FIG. 1B as degrees of curvature between C1 and C2 (such as below 5, 10, or 15 degrees)—upon being subjected to a first physical parameter within a first range of physical parameters indicative of a first physiological state. Implantable apparatus 102 may be configured to exhibit a second form within a second range of forms—depicted in FIG. 1B as degrees of curvature between C3 and C4 (such as greater than 10, 15, or 20 degrees)—when subjected to a second physical parameter within a second range of physical parameters indicative of a second physiological state.

The first physiological state may be a healthy state, such as the absence of a systemic or localized infection; and the second physiological state may be a diseased state, such as for example a hypothermic condition, or a localized or systemic infection. It will be appreciated that physiological states other than the presence of hypothermic conditions or localized or systemic infections may be indicated by the form of implantable apparatus 102.

The first range of forms and the second range of forms may be separated by an intermediate range of forms indicative of an alternative or intermediate physiological state. For example, implantable apparatus 102 may be configured to exhibit an intermediate range of forms between degree of curvature C2 and degree of curvature C3 when subjected to an intermediate range of physical parameters.

For example, embodiments of implantable apparatus 102 may be configured to facilitate the diagnosis of a localized or systemic infection. In such embodiments, implantable apparatus 102 may be configured to exhibit a degree of curvature between C1 and C2 (such as for example less than 5, 10, or 15 degrees) when subjected to temperature(s) within a baseline range of temperatures, such as a normal range of body temperatures. Such a baseline range of temperatures may be, for example, between 97 and 99 degrees Fahrenheit. And implantable apparatus 102 may be configured to exhibit a degree of curvature between C3 and C4 (such as for example greater than 10, 15, or 20 degrees) when subjected to temperature(s) within a temperature range indicating a systemic or localized infection, such as for example between 101 and 105 degrees Fahrenheit. This may leave an intermediate range of temperatures—between 99 and 101 degrees Fahrenheit—that corresponds to an intermediate range of degrees of curvature of implantable apparatus 102 between C2 and C3. Properties of implantable apparatus 102 may be selected such that a difference between C2 and C3 is sufficiently large to allow a difference between forms within the first range of forms to be discernable from forms within the second range of forms using an imaging technique, such as for example conventional imaging techniques, or other imaging techniques. The material type, thickness, or other properties of implantable apparatus 102 may be chosen such that forms within the first range of forms of implantable apparatus 102 is distinguishable or discernable from forms within the second range of forms of implantable apparatus using an imaging technique.

It will be appreciated that implantable apparatus 102 may be configured to indicate whether there is a fever, and therefore a localized or systemic infection. A "fever" may be defined as any temperature above 98.6 degrees Fahrenheit (or other temperature depending for example on the animal species in which implantable apparatus 102 is configured to be deployed). In embodiments, implantable apparatus 102 may not be configured to exhibit form or forms within an intermediate range of forms corresponding to an intermediate temperature range that is not indicative of any physiological state. In other words, there may be technically no temperature that is neither feverish nor non-feverish. Implantable apparatus 102 may, therefore, be configured to exhibit a straight form when subjected to 98.6 degrees Fahrenheit (or below), and any curvature of implantable apparatus 102 may indicate an increase in temperature from 98.6 degrees Fahrenheit, and may, therefore, indicate a fever and/or a localized infection. The greater the curvature, the more severe may be the fever indicated by implantable apparatus 102. In embodiments, implantable apparatus 102 may be configured to exhibit first forms within a first range of forms when there is no fever or only a slight fever (for example, up to 100 degrees Fahrenheit or other temperature), and to exhibit second forms within a second, discernibly different, range of forms above a certain threshold temperature, for example 101 degrees Fahrenheit or other temperature.

In embodiments where implantable apparatus 102 is configured to detect a hypothermic condition, implantable apparatus 102 may be configured to exhibit a degree of curvature between C1 and C2 when subjected to a baseline range of temperatures, such as a normal range of body temperatures. Such a baseline range of temperatures may be, for example, between 97 and 99 degrees Fahrenheit. And implantable apparatus 102 may be configured to exhibit a degree of curvature between C3 and C4 when subjected to a temperature range indicating a hypothermic condition, such as for example between 90 and 95 degrees Fahrenheit. This may leave an intermediate range of temperatures—between 95 and 97 degrees Fahrenheit—that corresponds to an intermediate range of degrees of curvature of implantable apparatus 102 between C2 and C3. Properties of implantable apparatus 102 may be selected such that a difference between C2 and C3 is sufficiently large to allow a difference between the first range of forms and the second range of forms to be discernable using an imaging technique, such as for example conventional imaging techniques, or other imaging techniques. For example, the material type, thickness, or other properties of implantable apparatus 102 may be chosen such that the first range of forms of implantable apparatus 102 is distinguishable or discernable from the second range of forms of implantable apparatus using an imaging technique.

It will be appreciated that implantable apparatus 100 of FIG. 1A may be configured to exhibit various forms when subjected to various physical parameters other than pressure, such as for example various temperatures or other physical parameter types. Similarly, it will be appreciated that implantable apparatus 102 of FIG. 1B may be configured to exhibit various forms when subjected to various physical parameters other than temperature, such as for example various pressures or other physical parameter types.

Implantable apparatuses 100 and/or 102 may exhibit a continuous range of sizes/shapes and a measured size or shape of an implantable apparatus may be correlated to a physical parameter. In some embodiment, the extent of the change of the form of the implantable apparatus may be correlated to, such as be proportional to, or alternatively have some non-linear relationship to, the change in the physical parameter.

In embodiments, implantable apparatuses may include a sealed bellows and/or a bi-material strip as will be discussed in more detail below.

Figure 2A:
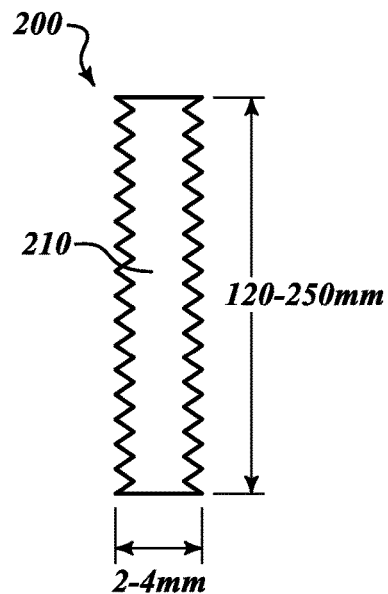
FIGS. 2A and 2B illustrate an implantable apparatus having a bellows configuration.
Figure 2B:
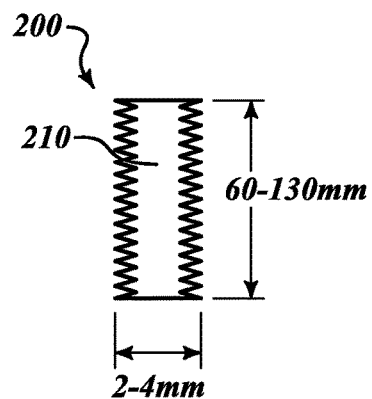

FIGS. 2A and 2B illustrate an implantable apparatus having a bellows configuration. Bellows 200 may be a sealed bellows column and may contain a compressible gas or fluid in interior area 210. Alternatively, bellows 200 may have a vacuum or near-vacuum within interior area 210. Bellows 200 may be configured to exhibit an elongated form as is shown in FIG. 2A; such elongated form may be within a first range of forms and bellows 200 may be configured to exhibit the elongated form when bellows 200 is subject to a physical parameter within a first range of physical parameters indicative of a first physiological state. Bellows 200 may be configured to exhibit a shortened form as is shown in FIG. 2B; such shortened form may be within a second range of forms and bellows 200 may be configured to exhibit the shortened form when subjected to a physical parameter within a second range of physical parameters indicative of a second physiological state. These physical parameters and physiological states may be as described elsewhere within this Detailed Description; they may alternatively be other physical parameters and physiological states not described herein without departing from the scope of embodiments.

A width of bellows 200 may be, in embodiments, between 2 and 4 millimeters. According to various embodiments, a first range of forms—such as an elongated form shown in FIG. 2A—may include lengths, for example, between 100 and 300 millimeters, or, for example, between 120 and 250 millimeters. According to various embodiments, a second range of forms—such as the shortened form shown in FIG. 2B—may include lengths, for example, between 50 and 150 millimeters, or, for example, between 60 and 130 millimeters. Bellows 200 may, for example, be configured to exhibit a shortened form that is roughly half of an elongated form, or some other fraction of the elongated form. Bellows 200 may be configured to exhibit other ranges of lengths, or have other widths, without departing from the scope of embodiments. The lengths and widths of embodiments of bellows 200 may be selected to allow catheter deployment of bellows 200, and/or to allow imaging of bellows 200 using conventional or non-conventional imaging techniques. Bellows according to embodiments may include metals, plastics, or other materials as discussed elsewhere within this Detailed Description.

The bellows depicted in FIGS. 2A-B has a body comprised of angular folds. It is to be understood that other bellows embodiments may be realized without departing from the scope of the present disclosure. For example, folds on a bellows body may be rounded. Alternatively, as shown in FIG. 2C, bellows according to embodiments may have a fin and groove structure.

Figure 2C:
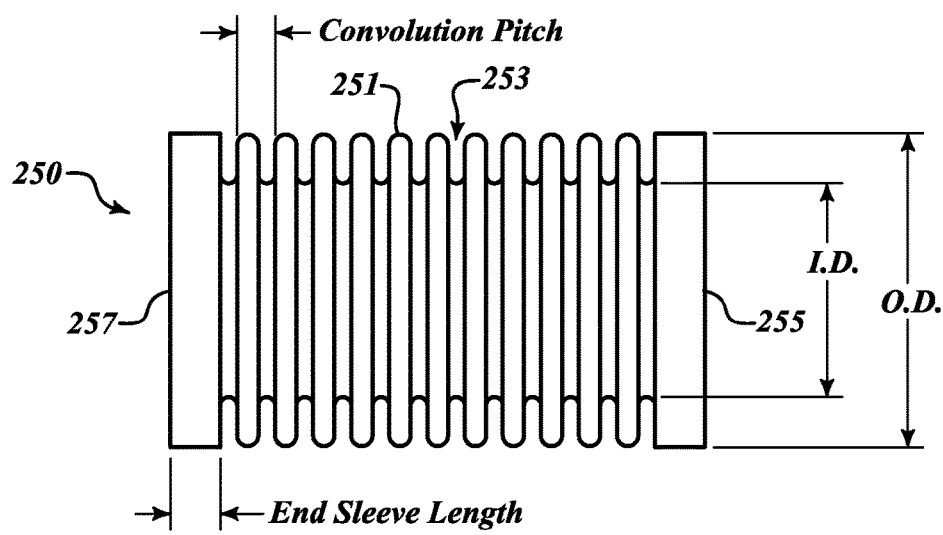
FIG. 2C illustrates an implantable apparatus having a bellows with a fin and groove structure.

FIG. 2C illustrates an implantable apparatus having a bellows with a fin and groove structure. Bellows 250 may include fins 251 and alternating grooves 253 along a body of the bellows. Bellows 250 may be sealed with end sleeves 255 and 257. Various attributes of bellows 250 may be engineered to have an appropriate response to the pressure ranges that bellows 250 may be expected to experience upon implantation into a localized area of an animal or human subject, as is described elsewhere within this Detailed Description. The outside diameter (O.D.), the inside diameter (I.D.), stroke volume, spring rate, convolution pitch, bellows material, convolutions length, number of convolutions, wall thickness, and overall length may each be individually selected to achieve appropriate responses to changes in pressure, as is described in more detail below.

Other than nickel alloy or stainless steel, bronze, brass, copper, silver, and gold may be used as the bellows material.

The pressure rating of bellows 250 may be given by the following formula:

$$P = \frac{1.25 \times 10^6 t^2}{(O - I - t)^2} \text{psi}.$$

Where O is the bellows outside diameter (O.D.), I is the inside diameter (I.D.), and t is the nominal wall thickness.

The stroke rating of bellows 250 may be given by the formula:

$$S = \frac{.0010(O - I - t)^2 N}{t}.$$

Where S is the number of inches of compression for 100,000 cycles life expectancy. Because bellows 250 is not expected to undergo many compression cycles over its life, less attention may need to be paid to the bellow's stroke rating. In the specific example discussed below, for example, the bellows may exceed the recommended maximum stroke per convolution, but this may be acceptable since the bellows may not flex very many times over the course of its life. A bellows according to embodiments may be expected to compress and decompress only zero to five times over its life, depending on how frequently the stent graft in the human or animal subject is compromised and replaced/repaired without replacing the bellows with a new bellows. Bellows 250 may undergo additional compressions and decompressions if bellows 250 is tested prior to implantation.

The spring rate of the bellows may be given by the formula:

$$R = \frac{4.3E(O + I)t^3}{(O - I - t)^3 N} \text{psi}.$$

Where E is Young's modulus of elasticity for the bellows material in psi, O is the bellows outside diameter (O.D.), I is the inside diameter (I.D.), t is the nominal wall thickness, and N is the number of convolutions active in the bellows. This formula assumes that the bellows has parallel side walls; for bellows with stepped and V grooves (such as those shown in FIGS. 2A and 2B), the rate is 1/3 higher.

In a specific but non-limiting example, a nickel alloy may be selected for the bellows 250 body material. Bellows 250 may be sealed with a vacuum and have a 0.125" O.D. and a 0.075" I.D., with a desired stroke volume of 0.50" when compressed to 80 mmHg (about 1.5 pounds-per-square-inch (psi)). The maximum applied pressure is 5 psi. Having a wall thickness of 0.0010" with a desired spring rate of 3 lbs/inch would produce a bellows with 57 convolutions. Given each convolution length (pitch) at 0.014", the total unrestricted length of the bellows is 0.8". With appropriate ends, the device unrestricted length would be about 1 inch, which may be small enough to fit into a localized area of a human or animal subject, such as in a repaired abdominal aortic aneurysmal sac. The spring rate of the exemplary device is approximately linear over the desired aortic pressure range; if 80 millimeters of mercury pressure produces a 0.5 inch stroke, then when the device is subjected to 50 millimeters of mercury pressure (such as when the device is subjected to the lower range of human aortic pressures), the compressed length of the device may be approximately 0.7 inches (a length reduction of 0.3 inches); when the device is subjected to 150 millimeters of mercury pressure (such as when the device is subjected to the high end of aortic pressures), the compressed length of the device may reach its minimum length, which may be between 0.3 to 0.5 inches. Other example bellows are possible. For example, nickel alloy may be replaced with stainless steel by adjusting the wall thickness using a ratio of Young's modulus of nickel and steel. Larger or smaller bellows are also possible.

Figure 3A:
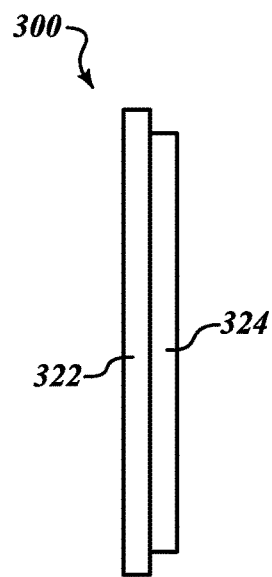
FIGS. 3A and 3B illustrate an implantable apparatus comprised of a bi-material strip.
Figure 3B:
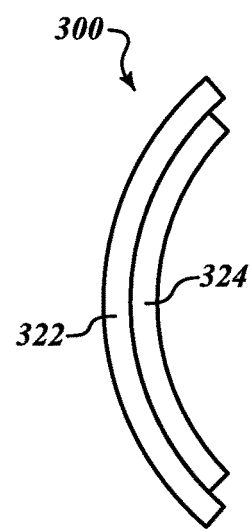

FIGS. 3A and 3B illustrate an implantable apparatus having a bi-material strip housing. Bi-material strip 300 may include first strip 322 and second strip 324 (different from the first strip), which may be attached to one another using adhesive, brazing, welding, rivets, screws, clamps, clips, or other suitable mechanisms. Examples of suitable materials are listed below, but generally, various metals and bio-compatible plastics may be used. Bi-material strip 300 may be configured to exhibit a relatively straight form, which may be within a first range of forms, when subjected to a first range of physical parameters indicative of a first physiological state, as is shown in FIG. 3A. Bi-material strip 300 may be configured to exhibit a curved form, which may be within a second range of forms, when subjected to a second range of physical parameters indicative of a second physiological state. These physical parameters and physiological states may be as described elsewhere within this Detailed Description; they may alternatively be other physical parameters and physiological states not described herein without departing from the scope of embodiments.

The two strips 322, 324 of bi-material strip 300 may each have differing responses to changes in temperature. For example, first strip 322 may be configured or selected to expand a relatively large amount in response to changes in physical parameters; conversely, second strip 324 may be configured or selected to expand a relatively small amount in response to changes in physical parameters. Alternatively, it may be first strip 322 that is configured to exhibit the relatively small response, and second strip 324 that is configured to exhibit a relatively large response. When subjected to a first range of physical parameters, one or both of first strip 322 and/or second strip 324 may exhibit a relatively straight form, with little or no curve. When subjected to a second range of physical parameters, expansion of first strip 322 may cause bi-material strip 300 to curve or bow inwards. Even though second strip 324 may normally remain relatively unchanged between the first and the second range of physical parameters, bi-material strip 300 may curve or bow inward due to adhesive forces between the first strip 322 the second strip 324 and the expansion of first strip 322. As described elsewhere within this Detailed Description, a degree of curvature of bi-material strip 300 may be imaged to facilitate an imaging diagnosis of a physiological state, such as the presence of a localized infection.

The curvature (κ) of bi-material strip 300 may be calculated as follows:

$$\kappa = \frac{6E_1 E_2 (h_1 + h_2) h_1 h_2 \epsilon}{E_1^2 h_1^4 + 4E_1 E_2 h_1^3 h_2 + 6E_1 E_2 h_1^2 h_2^2 + 4E_1 E_2 h_2^3 h_1 + E_2^2 h_2^4}.$$

Where E1 and h1 are the Young's Modulus and height of material one (of, for example, the first strip 322) and E2 and h2 are the Young's Modulus and height of material two (of, for example, the second strip 324). ε may be the misfit strain, calculated by:

$$\epsilon = (\alpha_1 - \alpha_2) \Delta T.$$

Where α1 may be the Coefficient of Thermal Expansion of Material One and α2 may be the Coefficient of Thermal Expansion of Material Two. ΔT may be a current temperature minus the baseline temperature, or the temperature where the bi-material strip has a straight orientation, such as for example a normal body temperature, or 98.7 degrees Fahrenheit.

Various materials can be used for the two strips. Suitable materials may include biocompatible metals and/or biocompatible plastics as discussed in more detail below. The greater the difference between coefficients of thermal expansion for the materials in a bi-material strip, the greater is the strip's sensitivity to temperature. Two suitable biocompatible metals, for example, may be stainless steel and aluminum which have a ratio of coefficients of about 16/22. In another example, a combination of stainless steel and acrylonitrile butadiene styrene (ABS) plastic increases the ratio spread to approximately 16/74, and using stainless steel and polyethylene plastic has a ratio of approximately 16/200. Generally, although non-metallic substances can be used, bi-metal strips may have greater long-term stability and lack of degradation than would strips that have non-metallic materials. For example, plastic strips may degrade over time when implanted into an animal or human subject.

In embodiments, various metals may be used to construct the implantable apparatus. Example metals include nitinol, titanium, stainless steel, various noble metals (such as ruthenium, rhodium, palladium, silver, osmium, iridium, platinum, gold). Each metal strip in a bi-metal strip may include a different metal, so as to result in differing responses to temperature. Such metals may be selected according to the desired temperature ranges envisioned.

An example bi-material strip 300 may be less than 1 mm in thickness and have a length of 0.75 inch or greater. An example bi-material strip 300 may exhibit a curvature of radius 1.5 to 2.5 inch when exposed to a feverish temperature, such as 101 degrees Fahrenheit or greater. An example bi-material strip 300 may have a length of 0.75 inch or greater.

The longer of the two strips may facilitate a determination of an orientation of a curve in bi-material strip 300 in order to distinguish a curve exhibited by bi-material strip 300 in response to physical parameters, from a curve exhibited by bi-material strip 300 in response to some other force. For example, bi-material strip 300 is shown in FIG. 3B bowed inward on the side of the shorter of the two strips, second strip 324. An image of bi-material strip 300 showing that bi-material strip 300 is bowed inward on the side of the longer of the two strips (first strip 322) may indicate that the bowing or bending is due to something other than a change in the physical parameters. It may, for example, indicate that bi-material strip 300 has been bent by some other mechanism, such as the formation of a blood clot within an aneurysmal sac.

In embodiments not shown in FIGS. 3A and 3B, bi-material strip 300 may be configured to exhibit a first range of forms that are curved inwards on the side of first strip 322 in response to a first range of physical parameters. In such embodiments, bi-material strip 300 may also be configured to exhibit a second range of forms that are curved in the other direction, on the side of second strip 324 in response to a second range of physical parameters (in a same or similar way as bi-material strip 300 is shown curved in FIG. 3B). In such an embodiment, a relatively straight form of bi-material strip 300 may be within an intermediate range of forms between the first and second ranges of forms.

Figure 3C:
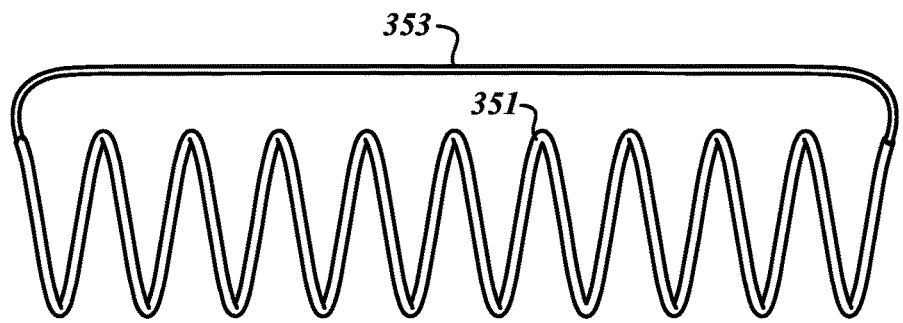
FIGS. 3C and 3D illustrate an implantable apparatus comprising a bi-material helical coil and an indicator wire.
Figure 3D:
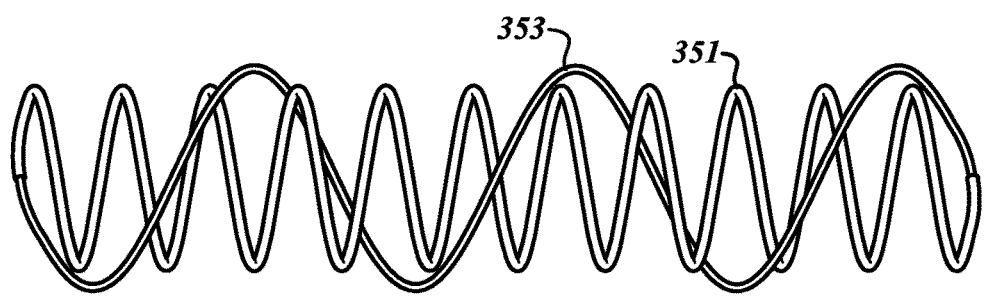

FIGS. 3C and 3D illustrate an implantable apparatus comprising a bi-material helical coil and an indicator wire. Bi-material helical coil wire 351 may be constructed out of various suitable materials. The ends of bi-material helical coil wire 351 may be connected with indicator wire 353, which may be a different wire that has been soldered, glued, adhered, or otherwise attached to bi-material helical coil wire 351. Alternatively, indicator wire 353 may be a segment of the same wire from which bi-material helical coil wire 351 is constructed. Assuming that ends on both sides of bi-material helical coil wire 351 are aligned at normal body temperature (a first physical state), inflammation-elevated temperature (a second physical state) would misalign the ends of bi-material helical coil wire 351 due to thermal expansion of one of the wires of bi-material helical coil wire 351. If the ends become misaligned due to temperature elevation, the initially-straight indicator wire 353 may twist around bi-material helical coil wire 351 as shown in FIG. 3D. Such twisting may be easily visible on X-Ray, MRI, CT scan. The angular rotation of a helical coil as shown in FIGS. 3C and 3D may be given by:

$$\alpha = \frac{2a(T-T_O)L}{s} \cdot \frac{360}{2\pi}.$$

Where $T-T_O$ is a temperature difference, L is the length of bi-material helical coil wire 351, where s is the thickness of bi-material helical coil wire 351, and a is the specific deflection of the material of bi-material helical coil wire 351. Certain polymers, having an appropriate temperature sensitivity at or around body temperature, may be used in order to achieve a desired rotational angle (for example at least 10° rotation), with a length that is appropriate for implantation into a small localized area, such as an abdominal aortic aneurysmal sac (for example no more than 5 inches in total length). An exemplary device may be composed of a polymer or other material in order to achieve a desirable sensitivity over the desired temperature ranges (such as between 98.7 degrees Fahrenheit to 101 degrees Fahrenheit).

Figure 3E:
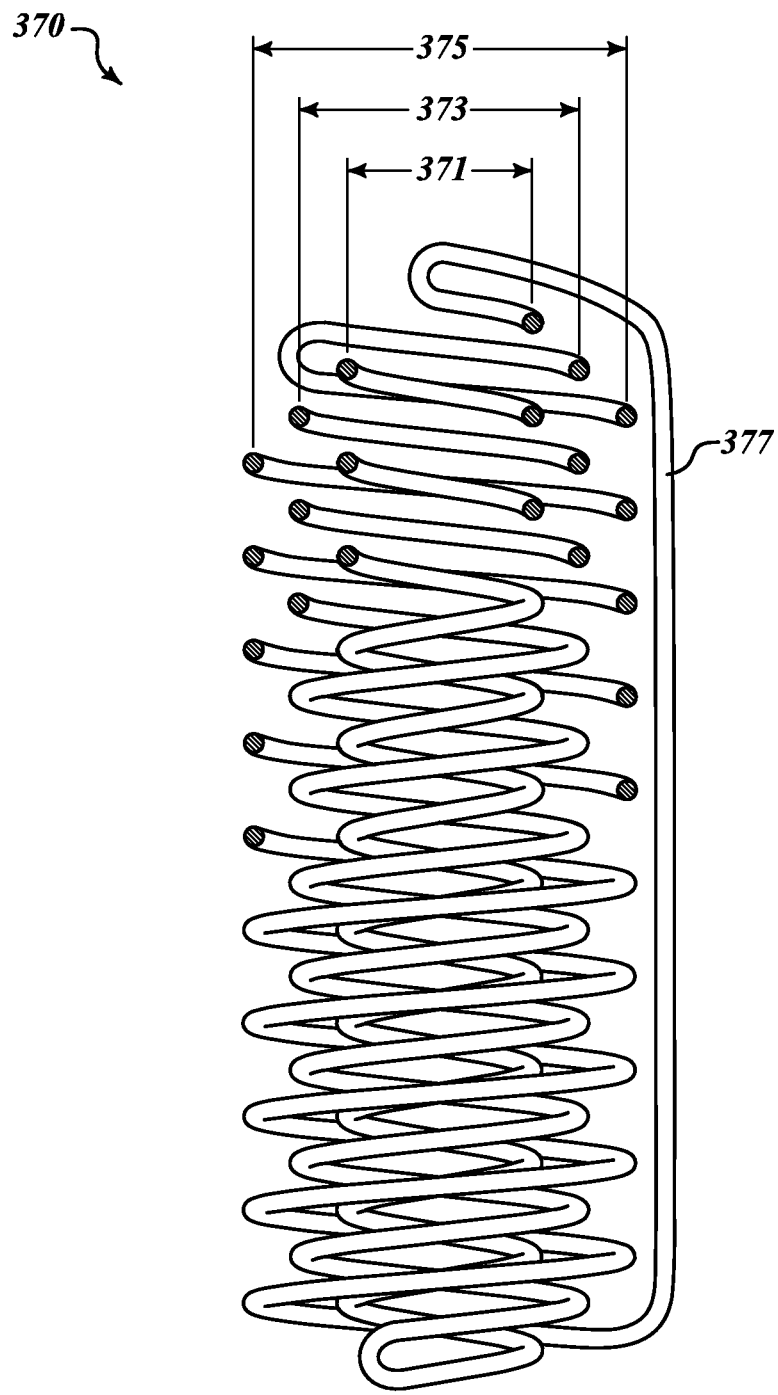
FIGS. 3E-3G illustrate implantable apparatuses comprising contiguous nested multiple helical coils and an indicator wire.
Figure 3F:
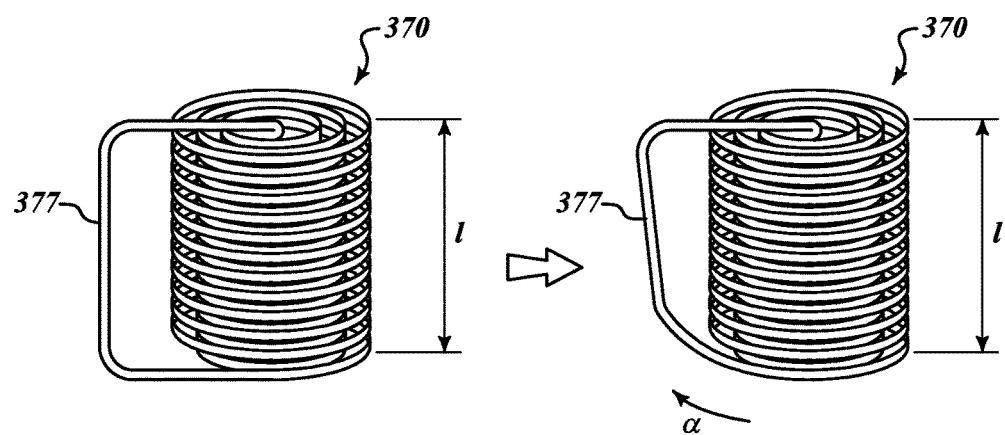
Figure 3G:
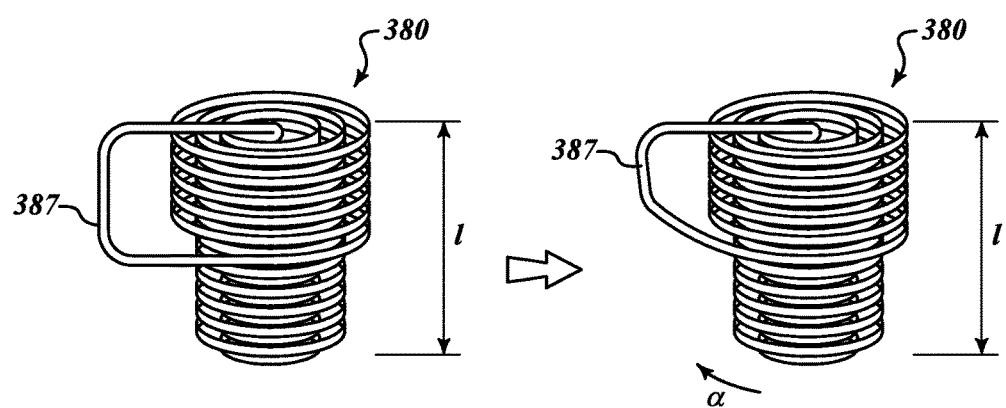

FIGS. 3E-3G illustrate implantable apparatuses comprising contiguous nested multiple helical coils and an indicator wire. FIG. 3E shows a schematic view of an implantable apparatus 370. Contiguous nesting multiple helical coils may be used to increase the temperature sensitivity and/or shorten the length of implantable apparatus 370 relative to embodiments illustrated in FIGS. 3C and 3D. Implantable apparatus 370 may be constructed out of various suitable materials, as are described above with respect to bi-material strip 300, and as described below in a specific example. A contiguous wire may be used to construct the entirety of implantable apparatus 370. Implantable apparatus 370 is shown with three contiguous nested helical coils, but up to fifteen (or more) coils may be used in other embodiments depending on the diameter of the largest helical coil (such as helical coil 375) as well as the width or diameter of the wire itself (not the width of the coil). In embodiments shown in FIG. 3E an odd number of nested helical coils may be used so that indicator wire 377 may span the length of implantable apparatus 370. An embodiment with an even number of coils could have an outer coil that spans less than the full length of implantable apparatus 370, as is discussed in more detail below.

Because each of helical wire coils 371, 373, and 375 are made of a contiguous piece of wire, they may all rotate in the same direction when implantable apparatus 370 is heated or cooled. Nesting each of helical wire coils 371, 373, and 375 results in an overall angular rotation for the ends of indicator wire 377 that may be estimated using the following formula:

$$\alpha = \alpha_{371} + \alpha_{373} + \alpha_{373} = (L_{371} + L_{373} + L_{375}) \cdot \frac{2a(T-T_O)}{s} \cdot \frac{360}{2\pi}.$$

Where $T-T_O$ is a temperature difference, $L_{371}$ is the length of inner helical coil 371, $L_{373}$ is the length of middle helical coil 373, and $L_{375}$ is the length of inner helical coil 375; s is the thickness of bi-material helical coil wire 351, and a is the specific deflection of the material of implantable apparatus 370. An overall length of the implantable apparatus may be the longest of $L_{371}$, $L_{373}$, and $L_{375}$. If $L_{371}$, $L_{373}$, and $L_{375}$ are the same length—as in FIG. 3E—then the overall length may be equal to $\frac{1}{3}^{rd}$ of the total contiguous wire coil length not including the indicator wire length (i.e., $\frac{1}{3}^{rd}$ of $L_{371}+L_{373}+L_{375}$).

In a specific example, if a 15° angular rotation is desired for a 2° C. temperature change from a baseline temperature (for example human body temperature of 37° C.) to a fevered temperature (for example 39° C.), KANTHAL 200 wire (which has a specific deflection of 20.8×10$^{-6}$ K$^4$) may be selected, with five nested helical coils. To achieve the desired 15° rotation with this arrangement, an overall coil length of 355 millimeters (approximately 12.4 inches) and 0.1 mm thickness may be used. Because there are five contiguous nested helical coils of the same length in this example, the overall length of the implantable apparatus is $\frac{1}{5}^{th}$ of 355 millimeters, or 71 millimeters (approximately 2.5 inches). If only a single helical wire coil were used (as in embodiments used in FIGS. 3C and 3D) the overall length of the apparatus would be 12.4 inches (using KANTHAL 200 wire), which may be impractical for certain applications, such as for use in an abdominal aortic aneurysmal sac that has been repaired with a stent/graft. Thus, using contiguous nested helical coils may shorten the overall length of the apparatus and/or increase its sensitivity.

FIG. 3F illustrates implantable apparatus 370 in a baseline form (indicating, for example, a "normal" or "healthy" temperature) as well as a rotated form (indicating, for example, a fever that may be indicative of localized inflammation). When implantable apparatus 370 is imaged with conventional imaging techniques as described elsewhere within this Detailed Description, the rotated form (shown rotated by angle α) may be discernable from the baseline form by a doctor, nurse, technician, clinician, or other person viewing the image, as is described elsewhere within this Detailed Description, to assist such person in diagnosing a localized inflammation, a fever, or other temperature-related physiological condition. In embodiments, a computer may be configured to perform computer-assisted comparison and analysis of the images to determine the presence of a physiological condition and/or the likelihood that a human or animal subject is experiencing, or has experienced, various physiological conditions.

Implantable apparatus 370 is shown in FIGS. 3E and 3F with three nested helical coils with roughly equal overall lengths and with indicator wire 377 that spans the length of implantable apparatus 370 (shown as/in FIG. 3F). In alternate embodiments illustrated in FIG. 3G, indicator wire 387 may span only a partial length of implantable apparatus 380. To accommodate this, an outside helical coil may have a shorter length than others of the nested helical wire coils that make up implantable apparatus 380. It may be preferable for the outside helical wire coil to be the shorter helical wire coil, but in alternate embodiments (not shown) the innermost helical wire coil may instead be the shorter coil. Note that embodiments shown in FIG. 3G may use either an even or an odd number of nested helical coils.

Due to the relatively short length of indicator wire 387 (compared to an indicator wire that spans the entire length/of implantable apparatus 380), the rotation of the ends of indicator wire 387 may be more pronounced than the rotation of implantable apparatus 370 shown in FIG. 3F, even though the two apparatus may be rotated by the same degree α. This is illustrated in FIGS. 3F and 3G. Both implantable apparatus 370 and implantable apparatus 380 have the same overall length l, and both are shown—in their rotated forms—rotated to the same degree α. But because indicator wire 387 is shorter than indicator wire 377, the wrapping of indicator wire 387 is more visibly pronounced than is the wrapping of indicator wire 377.

Assuming a rotational angle of 10°, length/of indicator wire 387 (or 377 as shown in FIGS. 3E-3G) may be between $1/4^{th}$ inch and ½ inch. Although the length/of indicator wire 387 may be shorter or longer, lengths longer than ½ inch may not result in a sufficiently pronounced wrapping with a rotation of only 10° and lengths shorter than $1/4^{th}$ inch may be too difficult to see in an image of the implantable apparatus. The higher the degree of rotation of the ends of indicator wire 387 (or 377) over a given temperature range, the longer may be the length of indicator wire 387 (or 377) without affecting viewability.

Figure 4:
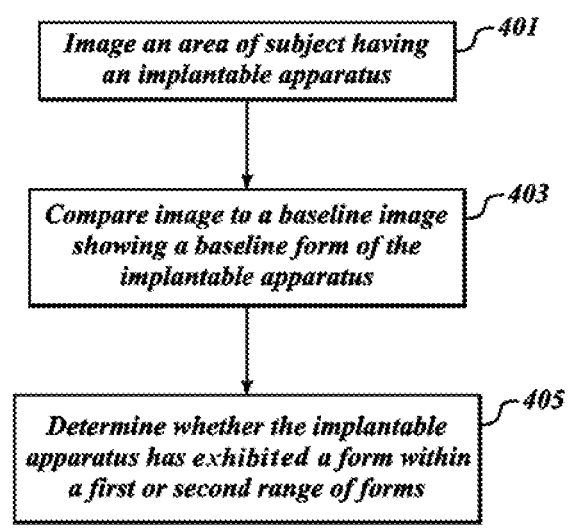
FIG. 4 illustrates a flow chart of a method of determining a physiological state of an animal or human subject by imaging an implantable biosensor.

FIG. 4 illustrates a flow chart of a method of determining a physiological state of an animal or human subject by imaging an implantable biosensor. An area of an animal or human subject may be imaged, block 401 ("Image an area of subject having an implantable apparatus"). An implantable apparatus as is described elsewhere within this Detailed Description may be present in the area. The area may be a localized area, and may be, for example, an area containing an abdominal or thoracic aortic aneurysm. The image may be compared to a baseline image showing a baseline form of the implantable apparatus, block 403 ("Compare image to a baseline image showing a baseline form of the implantable apparatus"). An image of the implantable apparatus taken after initial deployment of the implantable apparatus into the subject may be taken to create the baseline image. Alternatively, or in addition, the image may be compared to some other baseline image. Baseline images may depict the implantable apparatus during a time the implantable apparatus has been subjected to a known physiological condition inside the human or animal subject.

A determination may then be made as to whether the imaged implantable apparatus exhibits a first range of forms or a second range of forms, block 405 ("Determine whether the implantable apparatus has exhibited a form within a first or second range of forms"). The first range of forms may be indicative of a first range of physical parameters indicative of a first physiological state. The second range of forms may be indicative of a second range of physical parameters indicative of a second physiological state. Such ranges of forms, ranges of physical parameters, and physiological states may be those that are described elsewhere within this Detailed Description. In embodiments, the baseline image described above may show an implantable apparatus in the first range of forms, the second range of forms, or another range of forms (such as an intermediate range of forms) in order to provide a reference for determining the range of forms, if any, that the implantable device has exhibited in response to one or more physical parameters. Thus, comparison of the images may allow a computing device, or a person viewing the two images, to determine whether the form of the apparatus has changed, and whether the subject is, therefore, experiencing a different physiological state than when the baseline image was obtained. The materials, thicknesses, and other properties of implantable apparatuses according to embodiments may be selected to allow for such comparisons of the two images.

Though not depicted in FIG. 4, a determination may also be made as to whether an implantable apparatus contains fluid. In embodiments where the implantable apparatus is a sealed bellows (described in more detail elsewhere within this Detailed Description), an inside portion of the sealed bellows may contain a compressible gas or fluid. If the bellows becomes compromised, it may fill with blood or other bodily fluid and may no longer exhibit a form in response to physical parameters as originally configured. Thus, before a determination is made as to whether the implantable apparatus has exhibited a form within a first range of forms or a second range of forms, a determination may be made as to whether the bellows has been compromised, such as for example by determining whether fluid has entered the inside portion of the bellows. This determination may be made using ultrasound imaging, for example.

Figure 5:
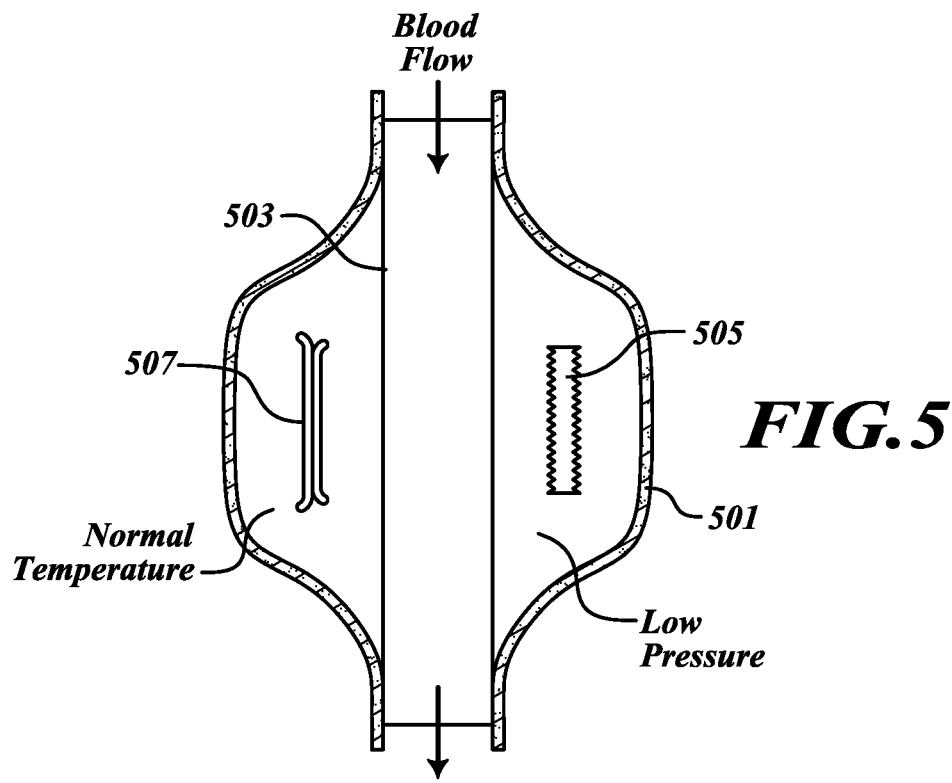
FIG. 5 illustrates a cross-section of an aneurysmal sac having a deployed stent/graft, a deployed implantable temperature sensor, and a deployed implantable pressure sensor according to various embodiments.

FIG. 5 illustrates a cross-section of an aneurysmal sac having a deployed stent/graft, a deployed implantable temperature sensor, and a deployed implantable pressure sensor according to various embodiments. FIG. 5 illustrates aneurysmal sac 501 in cross section, and with a deployed stent/graft 503. Blood may flow through stent/graft 503 as is indicated by the arrows in FIG. 5. Bellows 505 (which may be a pressure sensor) and Bi-material strip 507 (which may be a temperature sensor) may be present in aneurysmal sac 501. Bellows 505 may be in an elongated form which may indicate that there is low pressure within aneurysmal sac 501, which may, in turn, indicate that stent/graft 503 has not been compromised. Bi-material strip 507 may be in a straight form indicating that the temperature within aneurysmal sac 501 is normal, which may indicate that there is no localized infection. The individual strips of bi-material strip 507 may be composed of different types of biocompatible metals having differing responses to temperature. It will be appreciated that, in various embodiments, either one of bellows 505 or bi-material strip 507 may be deployed separately, depending on the need/desire to determine either the pressure or the temperature of aneurysmal sac 501. They are shown deployed together in FIG. 5 for ease of illustration.

Figure 6:
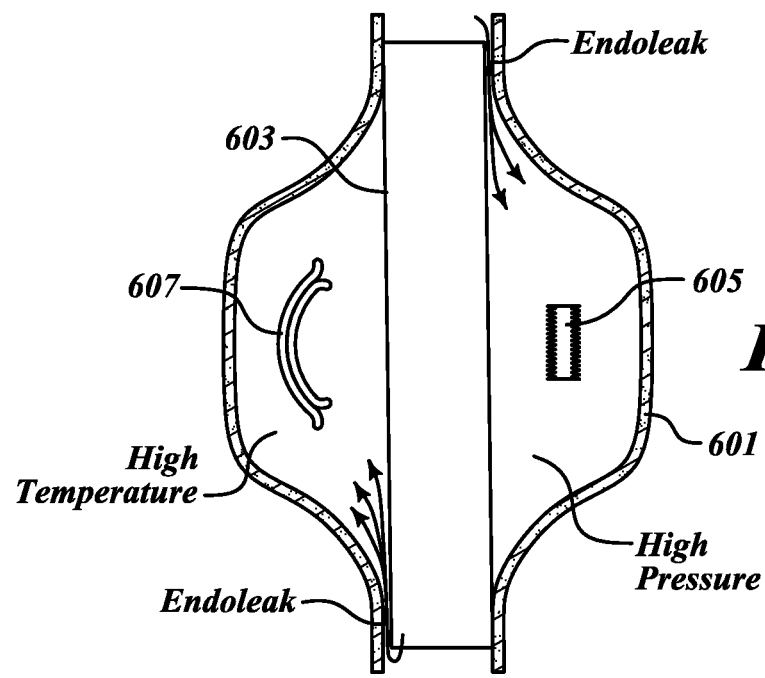
FIG. 6 illustrates a cross-section of an aneurysmal sac having a deployed stent/graft with an endoleak, a deployed implantable temperature sensor, and a deployed implantable pressure sensor according to various embodiments.

FIG. 6 illustrates a cross-section of an aneurysmal sac having a deployed stent/graft with an endoleak, a deployed implantable temperature sensor, and a deployed implantable pressure sensor according to various embodiments. FIG. 6 illustrates aneurysmal sac 601 in cross section, and with a deployed stent/graft 603. One or more endoleaks may have developed between aneurysmal sac 601 and stent/graft 603, as is shown by the arrows in FIG. 6. Bellows 605 and bi-material strip 607 may be present in aneurysmal sac 601. Bellows 605 may have a relatively shortened form. The relatively shortened form of bellows 605 may indicate the presence of high pressure (e.g., aortic pressure) within aneurysmal sac 601, which may be indicative of a physiological state such as the presence of the endoleaks or some other compromised condition of stent/graft 603. Bi-material strip 607 may be in a relatively curved state, which may be indicative of a high temperature within aneurysmal sac 601 (or the surrounding area generally), which may indicate a physiological state, such as a localized infection.

It is worth noting that the presence of a high temperature and the presence of a high pressure within aneurysmal sac 601 are not necessarily correlated. Stent/graft 603 may be compromised, thereby subjecting aneurysmal sac 601 and bellows 605 (along with bi-material strip 607) to vascular pressure, with or without the presence of a localized infection. Likewise, a localized infection may be present within the area of aneurysmal sac 601 thereby subjecting aneurysmal sac 601 and bi-material strip 607 (along with bellows 605) to an increased temperature, even though stent/graft 603 is not compromised. Alternatively, both physiological states may be present at the same time. Aneurysmal sac 601 is shown having both a localized infection and endoleaks in FIG. 6 for the ease of illustration.

The two strips of bi-material strip 607 may each have differing responses to temperature. For example, a first of the two strips may be configured to have a relatively greater response to temperature changes than the second of the two strips, at least over anticipated temperature ranges. When subjected to a "normal" temperature (for example 98.6 degrees Fahrenheit or similar temperature in a human subject), bi-material strip 607 may naturally exhibit a relatively straight form, with little or no curve. But when subjected to an elevated temperature, such as for example a temperature that may indicate a fever or localized infection, a first of the two strips may naturally expand. Even though the second of the two strips may normally remain relatively un-expanded over the elevated range of temperatures, bi-material strip 607 may curve or bow inward due to the coupling between the two strips. As noted previously, the two strips may be coupled using any suitable mechanism, including adhesive, brazing, welding, rivets, screws, clamps, clips, etc. As described elsewhere within this Detailed Description, a degree of curvature of bi-material strip 607 may be imaged to facilitate an imaging diagnosis of a physiological state, such as the presence of a localized infection.

The longer of the two strips may facilitate a determination of an orientation of the curve in bi-material strip 607, in order to distinguish a curve associated with a rise in temperature from a curve associated with some other physical bending of bi-material strip 607. For example, bi-material strip 607 is shown in FIG. 6 bowed inward on the side of the shorter of the two material strips. But an image of bi-material strip 607 showing that bi-material strip 607 is bowed inward on the side of the longer of the two strips may indicate that the bowing or bending is due to something other than an increase in temperature of aneurysmal sac 601. It may, for example, indicate that bi-material strip 607 has been bent by some other mechanism, such as the formation of a blood clot within aneurysmal sac 601. The strips of bi-material strip 607 may also have features on their ends as shown in FIG. 6 that may serve as another or an alternative reference point to help determine the relative orientation of a curve of bi-material strip 607.

Figure 7A:
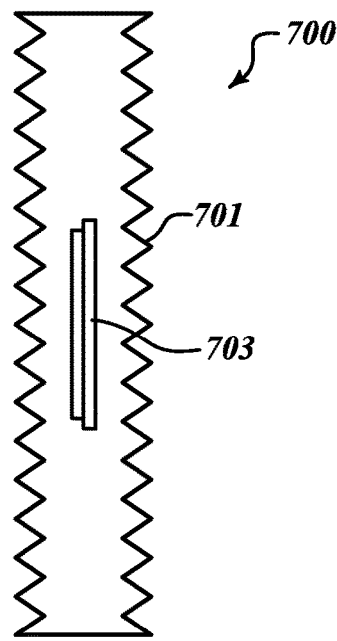
FIGS. 7A, 7B, and 7C illustrate an implantable apparatus having a form changeable upon exposure to various ranges of temperature and/or pressure.
Figure 7B:
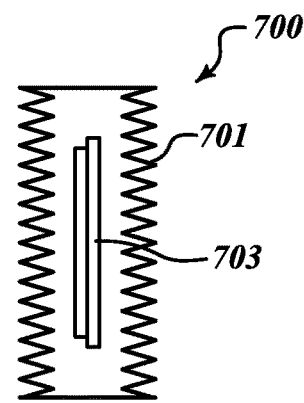
Figure 7C:
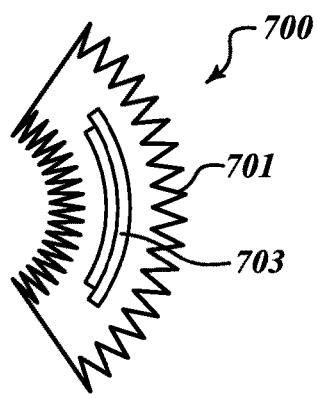

FIGS. 7A, 7B, and 7C illustrate an implantable apparatus having a form changeable upon exposure to various ranges of temperature and/or pressure. Implantable apparatus 700 may include a bellows 701. Within bellows 701 bi-material strip 703 may be present. Other than having bi-material strip 703 within it, bellows 701 may be configured as is described elsewhere within this Detailed Description. For example, bellows 701 may be configured to exhibit a shortened form responsive to an increase in external pressure—as is shown for example in FIG. 7B—relative to the elongated form of bellows 701 shown in FIG. 7A.

Bi-material strip 703 may be configured in a same or similar way as are other bi-material strips described elsewhere within this Detailed Description. For example, bi-material strip 703 may be configured to exhibit a relatively curved form responsive to an increase in pressure—as is shown in FIG. 7C—compared with the relatively straight form of bi-material strip 703 in FIG. 7A. When bi-material strip 703 exhibits a relatively curved form, it may cause bellows 701 to exhibit a bent shape as is shown in FIG. 7C. Thus, implantable apparatus 700 may be configured to facilitate a diagnosis of a localized infection by exhibiting a curved form as in FIG. 7C; implantable apparatus 700 may also be configured to facilitate diagnosis of an endoleak by being configured to exhibit a relatively shortened form as in FIG. 7B; and implantable apparatus 700 may also be configured to facilitate diagnosis of the presence of both a localized infection and an endoleak by simultaneously exhibiting both a bent and a shortened form.

In embodiments, bi-material strip 703 may be anchored to one end of bellows 701 in order to prevent a "jam" of bellows 701 by bi-material strip 703. Such a "jam" might prevent proper diagnosis of an endoleak by preventing bellows 701 from shortening responsive to an increase in pressure.

Embodiments are not limited to bellows and bi-material strips as have been described within this Detailed Description. An implantable spring-and-plunger apparatus will next be described.

Figure 8:
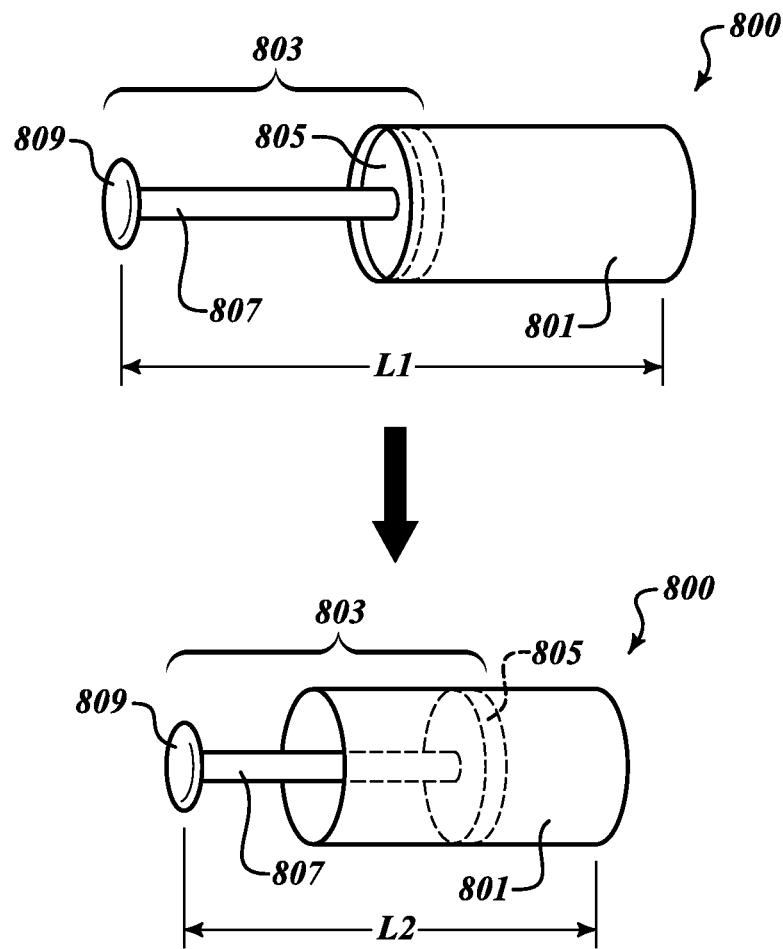
FIG. 8 illustrates an implantable spring-and-plunger apparatus for facilitating imaging-based diagnoses.

FIG. 8 illustrates an implantable spring-and-plunger apparatus for facilitating imaging-based diagnoses. Implantable apparatus 800 may include housing 801 and plunger 803. Plunger 803 may include seal end 805, shaft 807, and reference end 809. Housing 801 may have a compressible gas or fluid located internally, and the contact area between housing 801 and seal end 805 of plunger 803 may have a sufficient seal to prevent the compressible gas or fluid from escaping. When implantable apparatus 800 is subject to a relatively low pressure, the length between the end of housing 801 and reference end 809 may be L1 caused by a balance of forces of the compressible gas or fluid and the pressure external to implantable apparatus 800. When implantable apparatus 800 is subject to a relatively higher pressure, the compressible gas or fluid may be compressed, thereby moving plunger 803 down into a lower position within housing 801; in this case, the length between the end of housing 801 and reference end 809 may be L2. As is described elsewhere within this Detailed Description, implantable apparatus 800 may be imaged, and its length determined (such as for example by comparing the image to a reference or baseline image), to determine whether implantable apparatus 800 is subject to a relatively low or a relatively high pressure.

Figure 9:
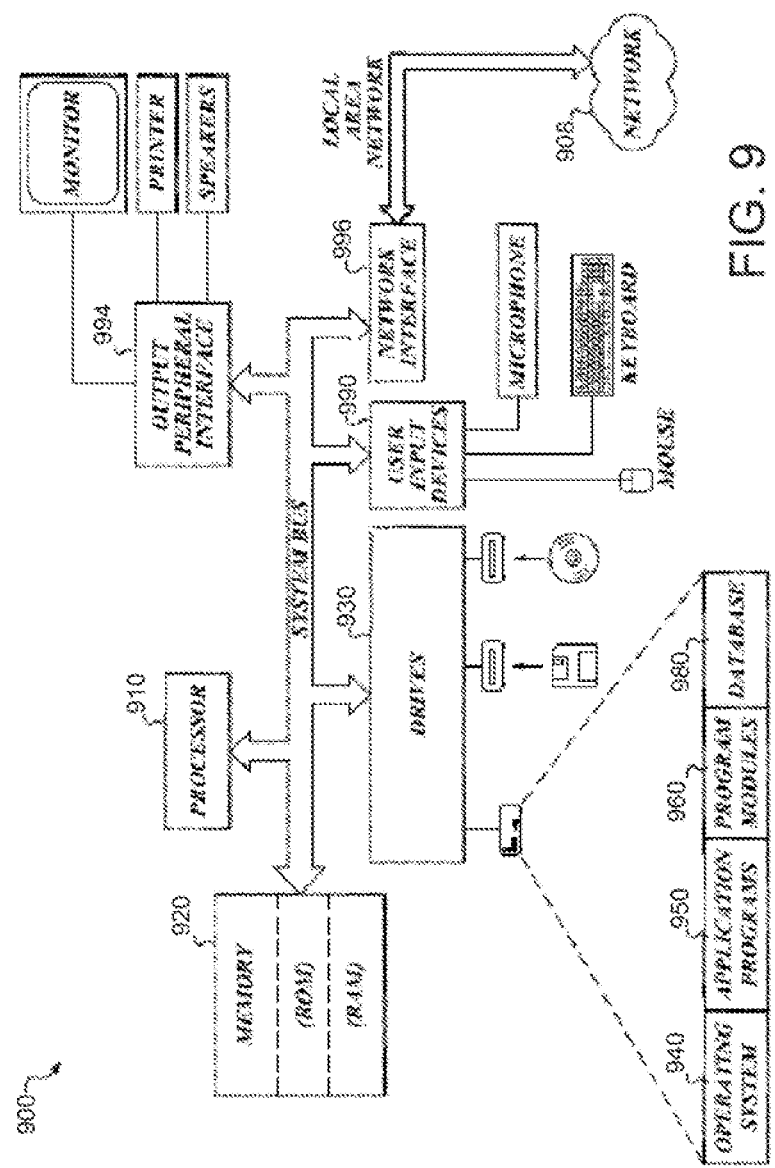
FIG. 9 illustrates a block diagram illustrating an example computing system, all arranged in accordance with various embodiments of the present disclosure.

FIG. 9 illustrates a black diagram illustrating an example computing system. FIG. 9 includes a computer 900, including a processor 910, memory 920 and one or more drives 930. The drives 930, and their associated computer storage media, provide storage of computer-readable instructions, data structures, program modules and other data for the computer 900. Drives 930 can include an operating system 940, application programs 950, program modules 960, and database 980. Computer 900 further includes user input devices 990 through which a user may enter commands and data. Input devices can include an electronic digitizer, a microphone, a keyboard and pointing device, commonly referred to as a mouse, trackball or touch pad. Other input devices may include a joystick, game pad, satellite dish, scanner, or the like.

These and other input devices can be connected to processor 910 through a user input interface that is coupled to a system bus, but which may be connected by other interface and bus structures, such as a parallel port, game port or a universal serial bus (USB). Computers such as computer 900 may also include other peripheral output devices such as speakers, printer, or monitor, which may be connected through an output peripheral interface 994 or the like.

Computer 900 may operate in a networked environment using logical connections to one or more computers, such as a remote computer connected to network interface 996. The remote computer may be a personal computer, a server, a router, a network PC, a peer device or other common network node, and can include many or all of the elements described above relative to computer 900. Networking environments are commonplace in offices, enterprise-wide area networks (WAN), local area networks (LAN), intranets and the Internet. For example, computer 900 may comprise the source machine from which data is being migrated, and the remote computer may comprise the destination machine or vice versa. Note however, that source and destination machines need not be connected by a network 908 or any other means, but instead, data may be migrated via any media capable of being written by the source platform and read by the destination platform or platforms. When used in a LAN or WLAN networking environment, computer 900 is connected to the LAN through a network interface 996 or an adapter. When used in a WAN networking environment, computer 900 typically includes a modem or other means for establishing communications over the WAN, such as the Internet or network 908. It will be appreciated that other means of establishing a communications link between the computers may be used.

One or more of operating system 940, application programs 950, program modules 960, and/or database 980 may include programming instructions or code configured to be executed on processor 910 and which, upon execution by processor 910, may cause computer 900 to perform various methods described herein, such as comparing two images of an implantable apparatus, a first of which may be a reference, comparison, or baseline image as described elsewhere within this Detailed Description, and a second of which may be an image of the implantable apparatus taken at some arbitrary time. Such comparison may determine if the current state of an implantable apparatus indicates that a human or animal subject (into which the implantable apparatus has been implanted) indicates that the human or animal subject is experiencing any of various possible physiological conditions. For example, computer 900 may be configured to determine that an implantable apparatus has shortened in length to indicate a relatively high pressure within a localized area of a human or animal subject. Computer 900 may also be configured to determine that an implantable apparatus has become curved or rotated to indicate a temperature change from a baseline or reference temperature within a localized area of a human or animal subject to a relatively high or relatively low temperature, to indicate a hypothermic or fever condition.

The herein described subject matter sometimes illustrates different components or elements contained within, or connected with, different other components or elements. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Various operations may be described as multiple discrete operations in turn, in a manner that may be helpful in understanding embodiments; however, the order of description should not be construed to imply that these operations are order-dependent. Also, embodiments may have fewer operations than described. A description of multiple discrete operations should not be construed to imply that all operations are necessary. Also, embodiments may have fewer operations than described. A description of multiple discrete operations should not be construed to imply that all operations are necessary.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the disclosure. Those with skill in the art will readily appreciate that embodiments of the disclosure may be implemented in a very wide variety of ways. This disclosure is intended to cover any adaptations or variations of the embodiments discussed herein. Therefore, it is manifestly intended that embodiments of the disclosure be limited only by the claims and the equivalents thereof.

What is claimed is:

1. An implantable device comprising:
    a bi-material helical coil wire having an indicator wire attached to both ends of the bi-material helical coil wire, wherein both ends of the bi-material helical coil wire remain aligned relative to one another when the implantable device is subjected to a first physical parameter such that the indicator wire remains substantially straight, and wherein both ends of the bi-material helical coil wire rotate relative to one another when the implantable device is subjected to a second physical parameter such that the indicator wire wraps around the bi-material helical coil wire.

2. The device of claim 1, wherein each end of the bi-material helical coil is attached to an opposite end of the indicator wire.

3. The device of claim 1, wherein the indicator wire is a segment of the bi-material helical coil.

4. The device of claim 1, wherein the bi-material helical coil comprises multiple bi-material helical coils in a contiguous nested configuration, and wherein the indicator wire spans a length of the multiple bi-material helical coils when subjected to the first physical parameter.

5. The device of claim 4, wherein each of the multiple bi-material helical coils in the contiguous nested configuration rotate in the same direction when subjected to the second physical parameter.

6. The device of claim 1, wherein the indicator wire remaining substantially straight is indicative of a first physiological state, wherein the indicator wire wrapping around the bi-material helical coil wire is indicative of a second physiological state, wherein the first physiological state is a healthy state, and wherein the second physiological state is a diseased state.

7. The device of claim 1, wherein the first physical parameter is a first temperature, and wherein the second physical parameter is a second temperature.

8. A method for determining a physiological state of an animal or human subject, comprising:
    analyzing, by a computing device, images of an area of the animal or human subject, wherein an implantable device is implanted in the area, wherein the implantable device comprises a bi-material helical coil wire having an indicator wire attached to both ends of the bi-material helical coil wire, wherein the implantable device is configured to have a first form indicative of a first physical parameter that is indicative of a first physiological state, and is configured to have a second form indicative of a second physical parameter that is indicative of a second physiological state, and wherein the first form is different from the second form;
    determining, by the computing device, whether the implantable device exhibits the first form or the second form by comparing a first image of the area of the animal or human subject to a second image of the animal or human subject, wherein the first form is based on a response to the first physical parameter, and wherein the second form is based on a response to the second physical parameter; and
    determining, by the computing device, whether the area of the animal or human subject is healthy or diseased based on whether the implantable device exhibits the first form or the second form, wherein the first form is a healthy state and the second form is a diseased state.

9. The method of claim 8, further comprising comparing an image of the area to a baseline image showing a baseline form of the implantable device.

10. The method of claim 8, wherein the first form is a first size and the second form is a second size.

11. The method of claim 8, wherein the first form is within a first range of forms, wherein the first range of forms is below a threshold value for the healthy state, and
    wherein the second form is within a second range of forms, wherein the second range of forms is above a threshold for the diseased state.

* * * * *

UNITED STATES PATENT AND TRADEMARK OFFICE
CERTIFICATE OF CORRECTION

| | |
|---|---|
| PATENT NO. | : 9,717,420 B2 |
| APPLICATION NO. | : 13/128627 |
| DATED | : August 1, 2017 |
| INVENTOR(S) | : Leschinsky et al. |

Page 1 of 1

It is certified that error appears in the above-identified patent and that said Letters Patent is hereby corrected as shown below:

In the Specification

In Column 20, Line 47, delete "Bi-material" and insert -- bi-material --, therefor.

In Column 22, Line 66, delete "a black" and insert -- a block --, therefor.

In Column 24, Line 45, delete "recitation no" and insert -- recitation, no --, therefor.

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*